United States Patent [19]
Dunks et al.

[11] Patent Number: 4,803,254
[45] Date of Patent: Feb. 7, 1989

[54] VINYLSILYLALKOXY ARYLBENZOTRIAZOLE COMPOUNDS AND UV ABSORBING COMPOSITIONS MADE THEREFROM

[75] Inventors: Gary B. Dunks, Upland; Akira Yamada, Claremont; Namassivaya Doddi, Upland, all of Calif.; Charles D. Beard, Montchanin, Del.

[73] Assignee: Iolab Corporation, Claremont, Calif.

[21] Appl. No.: 24,638

[22] Filed: Mar. 11, 1987

[51] Int. Cl.$^4$ .................... C08F 283/12; C08F 30/08
[52] U.S. Cl. .................................. 525/477; 526/261; 548/260; 623/6
[58] Field of Search ............... 548/260; 526/261, 279; 623/6; 525/477

[56] References Cited
U.S. PATENT DOCUMENTS
4,528,311  7/1985  Beard ..................... 524/91

Primary Examiner—Christopher Henderson
Attorney, Agent, or Firm—Charles J. Metz

[57] ABSTRACT

Vinylsilylalkoxy arylbenzotriazol monomers such as 2-[3'-t-butyl-5'-(3-'''-dimethylvinylsilylpropoxy)-2'-hydroxy-phenyl]-5-methoxybenzotriazole are disclosed. These monomers can be incorporated in optically clear silicone polymers to form intraocular lenses, contact lenses, and the like, which have UV absorbing properties.

12 Claims, 5 Drawing Sheets

VINYLSILYLALKOXY ARYLBENZOTRIAZOLE COMPOUNDS AND UV ABSORBING COMPOSITIONS MADE THEREFROM

The invention relates to certain vinylsilylalkoxy arylbenzotriazole monomers and to ultraviolet absorbing compositions made therefrom.

BACKGROUND OF THE INVENTION

The absorption of radiation in the ultraviolet range by polymeric materials is a major cause of the light-induced degradation therein. It is standard practice to add a low molecular weight UV "stabilizer" to light-sensitive polymers to absorb the light in the destructive range or to quench the energy generated as a result of the excitation of the light-absoring functional groups in the polymer.

Although low molecular weight VU absorbers or quenchers of various types are effective in inhibiting or retarding the destruction of the polymers to which they are added, their extractability in various media and/or their volatility during the processing for fabrication of the polymers at elevated temperatures place a limitation on their utility.

This problem has been remedied to a considerable extent by the synthesis of copolymerizable monomers containing structural moieties capable of functioning as UV absorbers or quenchers. The copolymerization of such monomers results in the formation of copolymers with increased stability, i.e., resistance to degradation upon exposure to UV light, with decreased extractability and volatility. The addition of such polymers to a suitable matrix polymer imparts these properties to the latter. U.S. Pat. No. 4,304,895 discloses the use of 2-hydroxy-4-methacryloyloxybenzophenone and mixtures thereof as a monomeric ultraviolet light absorber copolymerizable with acrylic monomers and useful in the preparation of UV absorbing hard contact lenses.

Similarly, the copolymerization of an allyl-2-hydroxy-benzophenone with an acrylate ester such as methyl methacrylate is described in the U.S. Pat. No. 4,310,650, and the copolymerization of ethylenically unsaturated derivatives of 2,4-dihydroxybenzophenone with other vinyl type comonomers is broadly disclosed in U.S. Pat. No. 3,162,676.

U.S. Pat. No. 3,213,058, to Boyle et al., discloses certain benzotriazole compounds and their incorporation into certain plastics, via reaction with carboxy and hydroxy groups contained in said compounds, as UV absorbers.

U.S. Pat. No. 4,528,311 discloses certain benzotriazole monomers which are copolymerizable with vinyl monomers such as methyl methacrylate to yield optically clear polymers useful in the preparation of intraocular and contact lenses. Representative of the disclosed bezotriazole monomers and a particularly preferred compound is 2-[3'-t-butyl-2'-hydroxy-5'-(3''-methacryloylozypropyl)phenyl]-5-chlorobenzotriazole, which has the structure:

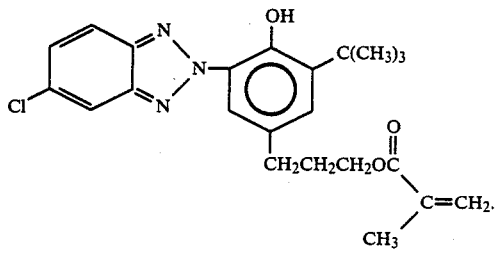

UV absorbing lenses are particularly desirable for use by persons who have had their natural lenses surgically removed owing to cataracts or other deterioration of the lens. The visual correction of aphakia resulting from such lens removal requires the use of high plus corrective lenses, which may be in the form of spectacles, contact lenses, or intraocular lenses.

In the normal eye, a portion of incident light entering the eye is absorbed by various parts of the eye so that only the unabsorbed or transmitted portion strikes the retina. Incident light may comprise the entire spectrum of wavelengths including the ultraviolet, visible, and infrared.

The cornea preferentially absorbs the ultraviolet portion of the light with wavelengths up to about 300 nm (nanometers). The crystalline lens preferentially absorbs ultraviolet light with wavelengths from about 300 up to about 400 nm. In the aphakic eye, where there is no crystalline lens, light having a wavelength higher than 300 nm will be transmitted directly to the retina, and the total spectrum of the light striking the retina in the aphakic eye will be different from that in the normal eye. As a consequence, aphakic patients are very sensitive to light in the ultraviolet range and may experience discomfort or color confusion when exposed to natural light or artificial light having high levels of ultraviolet wavelengths.

Inctrocular lenses and hard contact lenses are presently produced from methyl methacrylate polymers, which exhibit a combination of properties desirable for such products, particularly optical clarity, the capability of being cut and polished to specific optical powers, and chemical inertness.

Modern surgical techniques require an incision of only 2-3 mm for removal of the natural cataractous lens. however, the incision must be enlarged to permit the insertion of the PMMA intraocular lenses in use today. With a larger incision, the possibility of irregular closure and faulty apposition is increased, thereby increasing the possibility of developing astigmatism or other visual aberration as a result of the surgery. One proposed solution to the problem of undesired enlargement of the incision is the use of flexible intraocular lenses that can be inserted in a compressed condition, but which will assume their original shape after fixation in the eye. Silicone polymers possess the necessary flexibility to be used for this purpose, and are therefore being developed for use as intraocular lenses.

This invention provides certain monomers that are compatible with silicone polymers, and which can be incorporated in silicone polymers through covalent bonding to impart ultraviolet light absorbing properties to the silicone polymers containing the monomers.

The silicon containing monomers of the invention are incorporated in silicone polymers through the reaction of olefinic unsaturation in the silicone containing monomer with SiH groups in the silicone polymer. Non-silicon containing monomers containing olefinic unsaturation are capable of reacting in the same way; however, because of enhanced compatibility of the silicon containing monomers with the silicone polymers, compared with compatibility of non-silicon containing monomers with silicone polymers, there is a more complete reaction with the silicone polymer when the monomer contains silicon, which leads to a lower proportion of extractable non-reacted monomer. It is quite desirable for a device designed to be implanted in the living body to have as low an extractable content as possible.

BRIEF SUMMARY OF THE INVENTION

The vinylsilylalkoxy arylbenzotriazole monomers provided by the invention are compounds that are represented by Formula I:

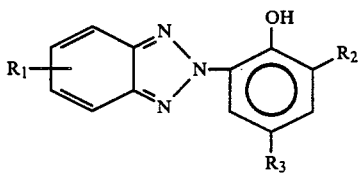

wherein $R_1$ and $R_3$ individually represent hydrogen, halo, alkoxy of from 1 to 6 carbon atoms, or X, wherein $R_2$ represents hydrogen or alkyl of up to six carbon atoms, and wherein X represents a group of the formula:

$$-O-R'-Si(R'')_2CH=CH_2 \qquad II$$

wherein R' represents alkylene of from 1 to 10 carbon atoms, and wherein each R'' individually represents alkyl of up to 4 carbon atoms or aryl, provided that one, and only one, of $R_1$ or $R_3$ represents X.

The invention also includes optically clear silicone polymers which incorporate the monomer represented by Formula I in an amount sufficient to impart ultraviolet light absorbing properties.

DETAILED DESCRIPTION OF THE INVENTION

The vinylsilylalkoxy arylbenzotriazole monomers of the invention are those that are represented by Formula I:

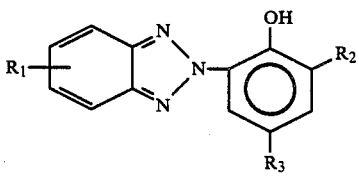

wherein $R_1$ and $R_3$ individually represent hydrogen, halo, alkoxy of from 1 to 6 carbon atoms, or X, wherein $R_2$ represents hydrogen or alkyl of up to 6 carbon atoms, preferably t-alkyl of from 4 to 6 carbon atoms, and wherein X represents a group of formula:

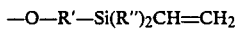

$$-O-R'-Si(R'')_2CH=CH_2 \qquad II$$

wherein R' represents alkylene of from 1 to 10 carbon atoms, and wherein each R'' individually represents alkyl of up to 4 carbon atoms or aryl, preferably phenyl, provided that one, and only one, of $R_1$ or $R_3$ represents X.

Figure 2A:
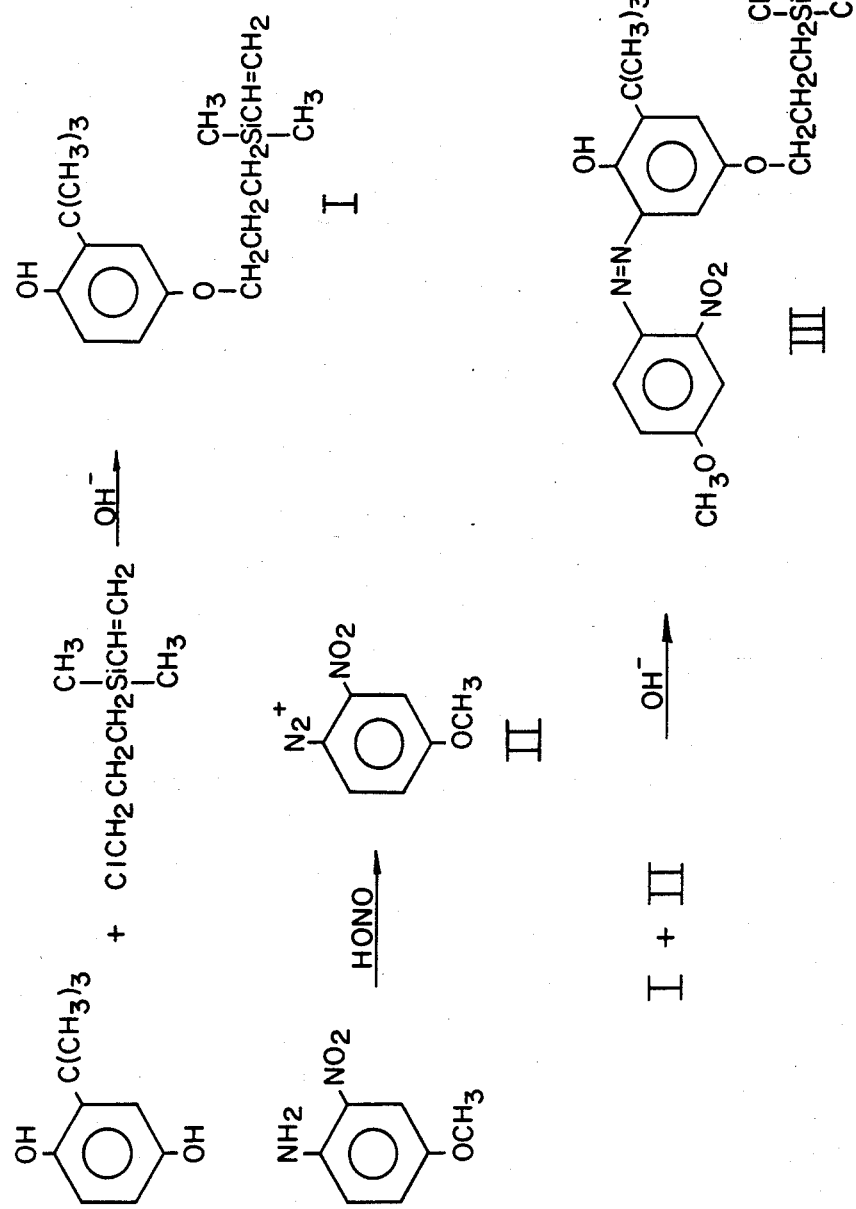
FIGS. 2a, 2b, 3a, and 3b show sequences of reactions that can be used to produce the vinylsilylalkoxy arylbenzotriazole monomers of the invention.
Figure 2B:
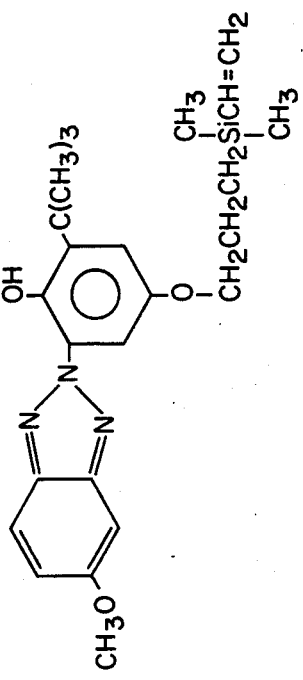

FIGS. 2a and 2b show a sequence of reactions that can be employed to produce the compounds represented by Formula I when $R_3$ is X. A summary of the sequence of reactions displayed in FIGS. 2a and 2b is the following:

In the first reaction shown, t-butylhydroquinone is reacted with chloropropyldimethylvinylsilane in a conventional Williamson ether synthesis to form 2-t-butyl-4-(3'-dimethylvinylsilylpropoxy)phenol (I).

In place of the t-butylhydroquinone, there may be employed other hydroquinones such as hydroquinone, methylhydroquinone, isopropylhydroquinone, and other alkylhydroquinones wherein the alkyl group has up to 6 carbon atoms. Preferably, the alkyl group is a tertiary alkyl group of from 4 to 6 carbon atoms. In place of the chloropropyldimethylvinylsilane there may be employed other silanes such as chloromethyldimethylvinylsilane and chlrorpropyldiphenylvinylsilane.

In the second reaction shown, 4-methoxy-2-nitroaniline is diazotized by reaction with HONO (which may be generated in situ by interaction of alkali metal nitrite with acid) to form the diazonium derivative, 4-methoxy-2-nitrobenzene-diazonium ion (II). In place of the 4-methoxy-2-nitroaniline, there may be employed 2-methoxy-6-nitroaniline, 2-nitroaniline, 4-chloro-2-nitroaniline, and other 4-alkoxy-2-nitroanilines wherein the alkoxy group has up to 6 carbon atoms.

In the next reaction, I is reacted with II to form the azo compound III, which is then cyclized and reduced to form the vinylsilylalkoxy arylbenzotriazole monomer IV.

The preparation of one preferred monomer of the invention is illustrated in the following examples:

EXAMPLE 1

Preparation of 2-t-butyl-4-(3'-dimethylvinylsilylpropoxy)phenol (I).

A 500-mL, 3-neck flask fitted with mechanical stirring and an inert gas inlet topped reflux condenser, was charged with t-butylhydroquinone (BHQ) (25.0 g, 0.15 mol), 2-methoxyethanol (125 mL), water (125 mL) and potassium hydroxide pellets (9.5 g, 0.17 mol). The mixture was stirred under inert gas (argon; nitrogen could also be used) to effect solution, the chloropropyldimethyl-vinylsilane (25.0 g, 0.15 mol) was added in one portion. The red-amber solution was heated to the reflux temperature and was maintained at that temperature for 24 hours. The reaction mixture was cooled to 30° C., then poured into a separatory funnel containing saturated aqueous sodium chloride solution (100 mL) and toluene (200 mL). The reaction flask was washed with toluene (50 mL), and the washings were added to the separatory funnel. After vigorous agitation, the upper organic layer was separated. The lower aqueous layer was extracted with toluene (200 mL). The toluene fractions were combined and washed with water (3×100 mL), dried over anhydrous magnesium sulfate, filtered and stripped to oil (36.1 g) using a rotary evaporator (water aspirator, 70° C.). The oil was vacuum distilled (0.05 mm Hg). The product, I, was collected from 130° C. to 143° C., (28.9 g, 66% yield). It was 94.3% pure by G.C. The postulated structure of I was confirmed by IR and $^1$H NMR analyses.

EXAMPLE 2

Preparation of 4-methoxy-2-nitrobenzenediazonium chloride (II) and 2-t-butyl-4-(3'-dimethylvinylsilylpropoxy)-6-(4"-methoxy-2"-nitrophenylazo)phenol (III)

A 250-mL beaker fitted with magnetic stirring, and a thermometer was charged with 4-methoxy-2-nitroaniline (12.6 g, 0.075 mol) and hydrochloric acid (22 mL). The mixture was stirred and heated (about 45° C.) to produce a smooth, pink slurry. The slurry was cooled to 0° C. (ice-salt bath and the addition of ice directly to the mixture), then a solution of sodium nitrite (5.7 g, 0.08 mol) in water (15 mL) was added over 30 minutes while the reaction temperature was maintained below 0° C. for 60 minutes. Sulfamic acid (about 0.5 g) was added to destroy excess nitrous acid (negative starch/iodide test), then the mixture was filtered cold.

Meanwhile, a 1000-mL beaker fitted with mechanical stirring and a thermometer was charged with I (14.2 g, 0.05 mol) and reagent grade ethyl alcohol (200 mL). The mixture was stirred to effect solution, then a solution of potassium hydroxide (11.2 g, 0.20 mol) in water (50 mL) was added. The red solution was cooled to 0° C. (ice-salt bath and addition of ice directly to the mixture) and the diazonium ion solution from above and a solution of potassium hydroxide (8.4 g, 0.15 mol) in water (15 mL) were added simultaneously over 30 minutes. The reaction mixture was purple throughout the addition. The final pH was about 13. The purple mixture was added to a well stirred solution of hydrochloric acid (12 mL) in water (3000 mL) over 30 minutes. The red solid that separated was isolated by filtration and pressed as dry as possible. The moist cake weighed 46.2 g. A small sample (dried in vacuum) was 82% pure by HPLC. The postulated structure of III was confirmed by IR and $^1$H NMR analyses.

EXAMPLE 3

Preparation of 2-[3'-t-butyl-5'-(3"-dimethylvinylsilylpropoxy)-2'-hydroxyphenyl]-5-methoxybenxotriazole (IV).

A 500-mL, 3-neck flask fitted with mechanical stirring, an inert gas inlet and a thermometer was charged with crude azo compound III (46.2 g, 0.05 mol), and reagent alcohol (150 mL). The mixture was stirred under inert gas (argon) at ambient temperature to effect solution, then a solution of glucose (18.0 g. 0.10 mol) in 2N aqueous sodium hydroxide solution (150 mL) was added over 78 minutes. The solution was stirred at ambient temperature for 17.4 hours, then zinc dust (33.0 g, activated in water, 80 mL with hydrochloric acid, 2 mL) was added. The mixture was stirred for 4.2 hours, then filtered to remove zinc. The zinc was washed with hot reagent alcohol (100 mL). The washings were combined with the filtrate and the solution was poured into a separatory funnel containing saturated sodium chloride solution (200 mL), 1N hydrochloric acid (300 mL), and toluene (300 mL). The mixture was agitated vigorously, then the upper organic layer was separated. The aqueous layer was extracted with toluene (200 mL) and the toluene fracgtions were combined. The combined toluene fractions were washed with water (4×200 mL), dried over anhydrous magnesium sulfate, filtered, and stripped to oil (16.6 g) on a rotary evaporator (water aspirator, 70° C.). The oil was passed through an alumina column (5×20 cm) with hexane eluent. The first canary-yellow fraction was collected and stripped to a yellow solid on the rotary evaporator (12.9 g). The solid was dissolved in hot methanol (300 mL), filtered, and allowed to cool slowly. The entire solution solidified. The pale yellow crystalline solid was isolated by filtration and dried in vacuum to yield 9.6 g (15% based upon BHQ) of monomer IV (mp 80°-82° C., 99.2% pure by HPLC). The postulated structure of IV was confirmed by IR and $^1$H NMR analyses.

EXAMPLE 4

Preparation of 2-[2'-Hydroxy-3'-t-butyl-5'-(3"-dimethylvinylsilylpropoxy)-phenyl]-5-chlorobenzotriazole (XI)

A 200 mL beaker fitted with a magnetic stirring bar was charged with moist 4-chloro-2-nitroaniline (19.2 g, 0.07 mol of 62% material), water (35 mL), and sulfuric acid (14.7 g, 0.15 mol). The mixture was stirred at about 40° C. for 90 minutes then cooled to −2° C. (ice-salt bath and direct addition of ice). A solution of sodium nitrite (5.4 g, 0.08 mol) in water (20 mL) was added over 40 minutes while maintaining the temperature below 0° C. The mixture was stirred for an additional 30 minutes, then sulfamic acid (0.1 g) was added to destroy excess nitrous acid (negative starch/iodide test). The cold mixture was filtered and stored cold.

Meanwhile a 1000 mL, 3-neck flask fitted with mechanical stirring and an argon inlet, was charged with 2-t-butyl-4-(3'-dimethylvinylsilylpropoxy)phenol (I), (see Example 1, above) (14.6 g, 0.05 mol), reagent alcohol (215 mL), and a solution of KOH (12.1 g, 0.19 mol of 88% base) in water (54 mL). The solution was cooled to 0° C. (ice-salt bath) and the diazonium ion solution from above and a cold solution of KOH (12.8 g, 0.20 mol of 88% base) in water (13 mL) were added simultaneously over 45 minutes (maximum temperature was 5° C.). The mixture was stirred (0° C.) for an additional 45 minutes then poured slowly into a well stirred solution of water (3000 mL) and sulfuric acid (9.2 g, 0.09 mol).

The red mixture from above was filtered (40-60 μm glass frit) to isolate the sticky, dark red azo compound (filtrate pH=7). The azo compound was washed with water (500 mL) then returned to the original 1000 mL, 3-neck reaction flask equipped as above, and reagent alcohol (200 mL) was added. A solution of sodium hydroxide (2.0 g, 0.30 mol), glucose (18.0 g, 0.1 mol), and distilled water (125 mL) was added over 90 minutes (maximum temperature 30° C.); then the mixture was stirred at ambient temperature for 16 hours. Zinc dust (35.0 g) was stirred with 1N hydrochloric acid (35 mL) for 20 minutes, then, after decanting the supernatant liquid (pH=7), was added to the reaction flask. The mixture was stirred for 2 hours, when an additional increment of activated zinc (20.0 g, activated as above) was added. The mixture was slowly stirred at ambient temperature for 62 hours (weekend). The golden-brown mixture was diluted with water (350 mL), then filtered to isolate the solid precipitate together with the remaining zinc. The filter cake was washed with a hot solution of reagent alcohol (400 mL) and potassium hydroxide (20.0 g) in several increments to extract the product. The filtrate was slowly added to well stirred water (1400 mL). The solid precipitate was isolated by filtration, and then was dissolved in methylene chloride (200 mL). The solution was dried over anhydrous sodium sulfate, filtered, and stripped to oil (10.2 g) on a rotary evaproator (water aspirator). The oil was dissolved in hexane (20 mL), then introduced onto a silica-gel column (5×15 cm) and eluted with hexane. The first 1200 mL of eluent was collected and stripped to oil (3.5 g) on a rotary evaporator (water aspirator). The oil was dissolved in hot methanol (70 mL) and allowed to cool to ambient temperature and stand overnight. The golden-yellow, crystalline precipitate was isolated by filtration (4.2 g moist), then redissolved in hot methanol), boiled wiht decolorizing carbon (2 g) for 10 minutes, filtered through Celite ™, allowed to cool, then stored at 0° C. overnight. The yellow crystalline precipitate was isolated by filtration and dried in vacuum. The yield of XI was 0.9 g, mp 67°–90° C. (one spot on TLC). The postulated molecular structure of XI was confirmed by IR and $^1$H NMR analyses.

Figure 3A:
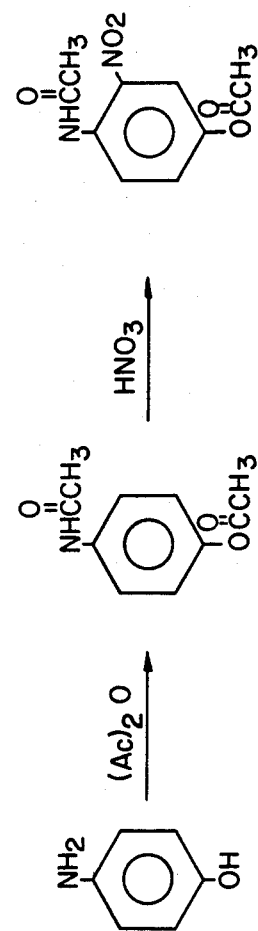
Figure 3A:
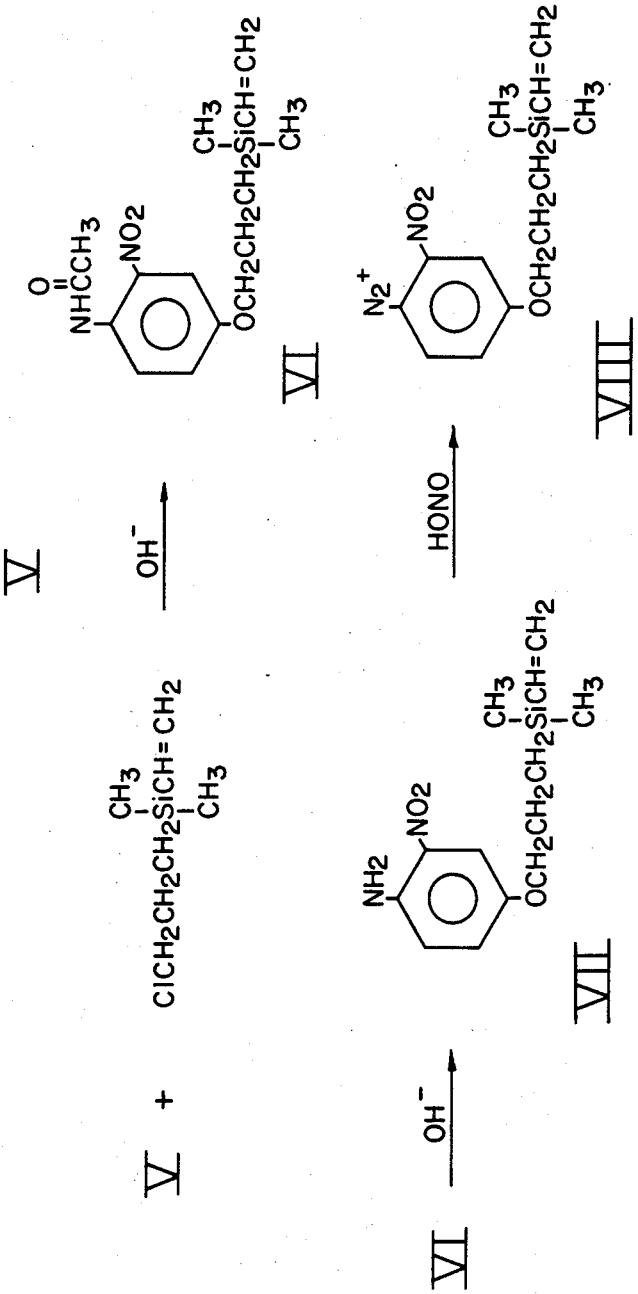
Figure 3B:
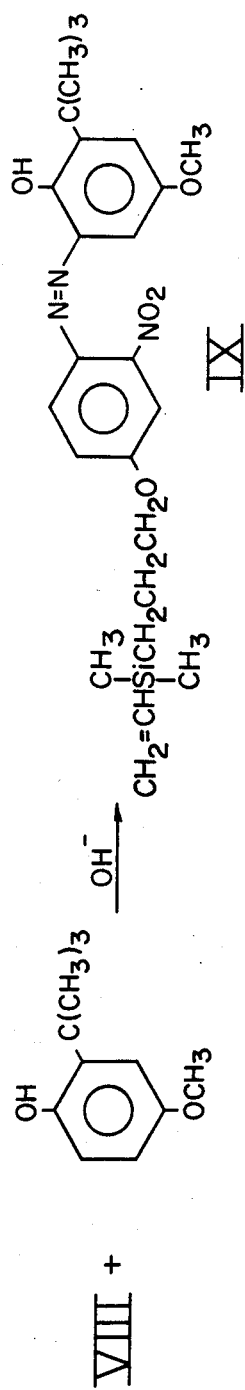
Figure 3B:
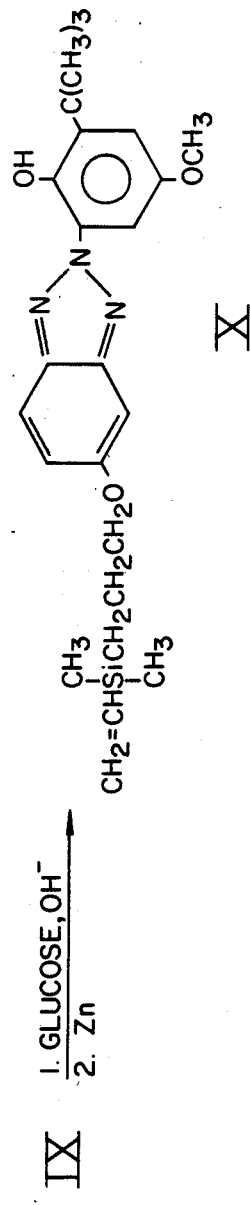

The foregoing Examples illustrate the preparation of the vinylsilylalkoxy arylbenzotriazole compounds of the invention wherein $R_3$ in Formula I is X. The compounds of the invention wherein $R_1$ in Formula I is X can be prepared by a sequence of reactions that is illustrated by the sequence shown in FIGS. 3a and 3b. A summary of the sequence of reactions shown in FIGS. 3a and 3b is the following:

Para-aminophenol is acetylated by reaction with acetic anhydride to form 4-acetoxyacetanilide, which is then nitrated to form 4-acetoxy-2-nitroacetanilide (V). V is then reacted with 3-chloropropyldimethylvinylsilane to form 4-(3'-dimethylvinylsilylpropoxy)-2-nitroacetanilide (VI). VI is hydrolyzed to form VII, which is then reacted with nitrous acid to form a 4-(3'-dimethylvinylsilylpropoxy)-2-nitrobenzenediazonium ion (VIII). The diazonium ion VIII is then reacted with 2-t-butyl-4-methoxyphenol to form 2-t-butyl-6-[4'-(3''-dimethylvinylsilylpropoxy)-2'-nitrophenylazo]-4-methoxyphenol (IX). The azo compound IX is then reacted with glucose and base, and then with zinc to form 2-(3'-t-butyl-2'-hydroxy-5'-methoxyphenyl)-5-(3''-dimethyl-vinylsilylpropoxy)benezotriazole (X).

In the foregoing reaction sequence, the chloropropyldimethylvinylsilane may be replaced with other silanes such as chloromethyldimethylvinylsilane, chloropropylmethylphenylsilane, and chloropropyldiphenylvinylsilane. In place of the 2-t-butyl-4-methoxyphenol there may be employed other phenols, such as, phenol, 2-t-butyl-4-chlorophenol, 4-chloro-2-methylphenol, 4-methoxyphenol, and the like.

The following examples illustrate the preparation of one preferred compound of the invention wherein $R_1$ in Formula I is X:

EXAMPLE 5

Preparation of 4-Acetozyacetanilide

A 500 mL, 3-neck flask fitted with mechanical stirrer, an inert gas inlet topped reflux condenser, and a thermocouple was charged with acetic acid (32 mL) and 4-aminophenol (10.9 g, 0.10 mol). Acetic anhydride (30.2 g, 0.30 mol) was added in one portion and the brown, clear solution was heated to 100°–110° C. and maintained at that temperature for 16 hours. Heating was stopped and the reaction mixture was allowed to cool slowly with stirring (under argon). After approximately 1 hour the mixture had cooled to 20° C. and precipitation began. The mixture was cooled to ~0° C. (ice-salt bath) and maintained at that temperature for 6 hours and was then filtered. The pale-pink solid was dried in vacuum to yield 16.1 g, 0.08 mol of 4-acetoxyacetanilide (mp 140°–142° C.). The molecular structure was confirmed by IR and $^1$H NMR analyses.

EXAMPLE 6

A 500 mL, Erlenmeyer flask equipped with a magnetic stirring bar and a thermocouple was charged with 4-acetoxyacetanilide (10.3 g, 0.05 mol), methylene chloride (50 mL), and acetic anhydride (16.2 g, 0.16 mol). The mixture was stirred at ambient temperature for 15 minutes (incomplete solution), and then was cooled to 0° C. (ice-salt bath). Nitric acid (5.0 mL, 0.08 mol, 70% acid, d=1.42) was added over a 30 second period. The ice bath was removed and the mixture was heated to boiling (42.5° C.) and maintained at that temperature for 30 minutes. The reaction temperature was slowly increased to 75° C. to distill methylene chloride, and then the mixture was allowed to cool slowly to ambient temperature and stand for 16 hours. The crystalline precipitate was isolated by filtration and vacuum dried to yield 7.1 g, 0.03 mol of 4-acetoxy-2-nitroacetanilide (mp 143°–146° C.). The structure of V was confirmed by IR and $^1$H NMR analyses.

EXAMPLE 7

Preparation of 4-(3'-Dimethylvinylsilylpropoxy)-2-nitroaniline (VII)

A 500 mL, 3-neck flask equipped with mechanical stirring, an inert gas inlet topped reflux condenser, and a thermocouple was charged with methoxyethanol (50 mL), potassium hydroxide (5.5 g, 0.09 mol of 88% base), and 4-acetoxy-2-nitroacetanilide (7.0 g, 0.03 mol). The purple mixture was stirred at ambient temperature for 60 minutes and then heated to and maintaained at reflux for 60 minutes. After cooling the mixture to 30° C., 3-chloropropyldimethylvinylsilane (7.2 g, 0.04 mol) was added in one portion. The mixture was heated to reflux and maintained at that temperature for 20 hours, and was then allowed to cool slowly with stirring. The mixture was filtered to remove potassium chloride, and then was stripped to brown tar (17.8 g) on a rotary evaporator. The tar dissolved in boiling acetone (150 mL). The acetone solution was cooled to ambient temperature, then silica gel (100 g, 80–100 mesh) was added. The mixture was stripped to dryness on a rotary evaporator, then was charged to a silica gel chromatography column (5×20 cm) and was eluted with methylene chloride. The initial red fraction (~1000 mL) was allowed to pass, then the second orange-red fraction was collected (~2000 mL). The orange-red solution was stripped to a red oil on a rotary evaporator. The oil (crystallized on standing) was dissolved in boiling reagent alcohol (200 mL), then water was added (20 mL). The clear, red solution was allowed to cool and stand at ambient temperature for 24 hours. The red needles were collected by filtration and dried in vacuum to yield 6.1 g of 4-(3'-dimethylvinylsilylpropoxy)-2-nitroaniline (mp 64.5°–66.5° C.). The structure of VII was confirmed by IR and $^1$H NMR analyses.

EXAMPLE 8

Preparation of
2-t-Butyl-6-[4'-(3"-dimethylvinylsilylpropoxy)-2'-nitrophenylazo]-4-methoxyphenol (IX)

A 400 mL beaker equipped with a magnetic stirring bar and a thermocouple was charged with 4-(3'-dimethylvinylsilylpropoxy)-2-nitroaniline (4.1 g, 0.015 mol), methanol (20 mL), water (10 mL), and hydrochloric acid (7.0 mL, 0.07 mol). The mixture was stirred at ambient temperature for 20 minutes (incomlete solution) and then cooled to 0° C. (ice-salt). A solution of sodium nitrite (2.2 g, 0.032 mol) in water (22 mL) was added over 1.7 hours. The mixture was stirred at 0° C. for an additional 30 minutes, the filtered (cold) to remove unreacted aniline (1.7 g, dry). The filtrate was stored cold.

Meanwhile, a 1000 mL beaker fitted with a magnetic stirring bar and a thermocouple was charged with 4-methoxy-2-tert-butylphenol (3.3 g, 0.018 mol), potassium hydroxide (3.0 g, 0.05 mol of 88% base), and water (133 mL). The mixture was stirred at ambient temperature for 30 minutes (incomplete solution) and then cooled to 0° C. by the direct addition of ice. The diazonium ion solution from above and a solution of potassium hydroxide (1.5 g, 0.022 mol of 88% base) in water (17 mL) were added simultaneously over 15 minutes. The mixture was maintained at ~0° C. throughout the addition by adding ice. The red mixture was stirred for an additional 30 minutes and then filtered to isolate the red solid precipitate (filtrate pH=14). The solid was washed with water (3×100 mL) then dried in vacuum to yield 3.3 g of 2-t-Butyl-6-[4'-(3"-dimethylvinylsilylpropoxy)-2'-nitrophenylazo]-4-methoxyphenol.

A small sample was dissolved in hot reagent alcohol and then water was added until cloudiness was just visible at the point of addition. The clear, dark red solution was allowed to cool to ambient temperature and stand for 2 days. The dark red needles were isolated by filtration and dried in vacuum to yield pure 2-t-Butyl-6-[4'-(3"-dimenthylvinylsilylpropoxy)-2'-nitrophenylazo]-4-methoxyphenol (mp 125°–129° C.). The structure of IX was confirmed by IR and $^1$H NMR analyses.

EXAMPLE 9

Preparation of
2-(3'-t-Butyl-2'-hydroxy-5'-methoxyphenyl)-5-(3"-dimethylvinylsilylpropoxy)benzotriazole (X)

A 100 mL, 3-neck flask equipped with a magnetic stirring bar, an inert gas inlet topped reflux condenser, and a thermocouple was charged with IX (3.3 g, 0.007 mol) and reagent alcohol (20 mL). The mixture was heated to 60° C. to aid solution, and then cooled to 20° C. (solution incomplete). A solution of glucose (2.5 g, 0.014 mol), sodium hydroxide (1.7 g, 0.043 mol), and distilled water (17 mL) was added over 30 minutes. The mixture was stirred at ambient temperature for 22 hours. Zinc dust (3.3 g, activated with 3 mL 1N hydrochloric acid) was added. After 25 minutes, an additional increment of zinc dust (3.5 g activated as above) was added. After approximately 1 hour, a yellow-tan precipitate began to form. The mixture was stirred for 5 hours and then filtered. The solid on the filter was washed with hot reagent alcohol (4×50 mL). The washings and filtrate were combined in a separatory funnel containing saturated sodium chloride solution (600 mL), 1N hydrochloric acid (100 mL), and toluene (100 mL). After vigorous agitation, the upper toluene layer was separated. The lower aqueous layer was extracted with toluene (50 mL). The combined toluene fractions were washed with water (2×75 mL), dried over anhydrous magnesium sulfate, and stripped to a brown oil on a rotary evaporator. The oil was dissolved in methylene chloride (20 mL) and then stripped onto alumina (20 g). The solid was charged to an alumina chromatography column (5×5 cm) and eluted with hexane.

The first, canary yellow, fraction was collected and stripped to oil (91.7 g) on a rotary evaporator. The oil was dissolved in hot methanol (60 mL), filtered, and then stored at 0° C. for 2 days. The solid was isolated by filtration and then dried in vacuum to yield 0.8 g of 2-(3-t-butyl-2'-hydroxy-5'-methoxyphenyl)-5-(3"-dimethylvinylsilylpropoxy)benzotriazole (mp 67°–69° C.). The structure of X was confirmed by IR and $^1$H NMR analyses.

The vinylsilylalkoxy arylbenzotriazole compounds of the invention can be reacted with silicone polymers and/or with silicon polymer-forming reactants that contain SiH moieties. The SiH moieties will react with the vinyl groups in an addition reaction in accordance with the following:

$$\equiv SiH + CH_2 = CH - \longrightarrow \equiv Si - CH_2 - CH_2 -$$

This is a known type reaction and those of ordinary skill in the art know how to carry out this type reaction. The presence of the silicon in the monomers of the invention enhance the compatibility of the monomers with the silicone ploymers or silicone polymer-forming reactants so that there is a minimum or unreacted or extractable monomer after the reaction. This is important in applications where the ultimate material is to be employed in contact with bodily tissue or implanted in a body, as would be the case with contact lenses or with intraocular lenses.

The examples set forth below illustrate the incorporation of the monomers of the invention in silicone polymers. The silicone polymer employed in the examples was a commercially available RTV (room temperature vulcanizable) polysiloxane material consisting of two parts. Part A was a polysiloxane oligomer contaiing dimethylsiloxane, diphenylsiloxane, and methylvinylsiloxane units. Part A also contained a platinum catalyst for the reaction of SiH silane groups with vinyl groups. Part B was an oligomer that contained dimethylsiloxane, diphenylsiloxane, and methylsiloxane units. The examples below give illustrative conditions for carrying out the incorporation of the monomers of the invention into an organopolysiloxane polymer.

EXAMPLE 10

Figure 1:
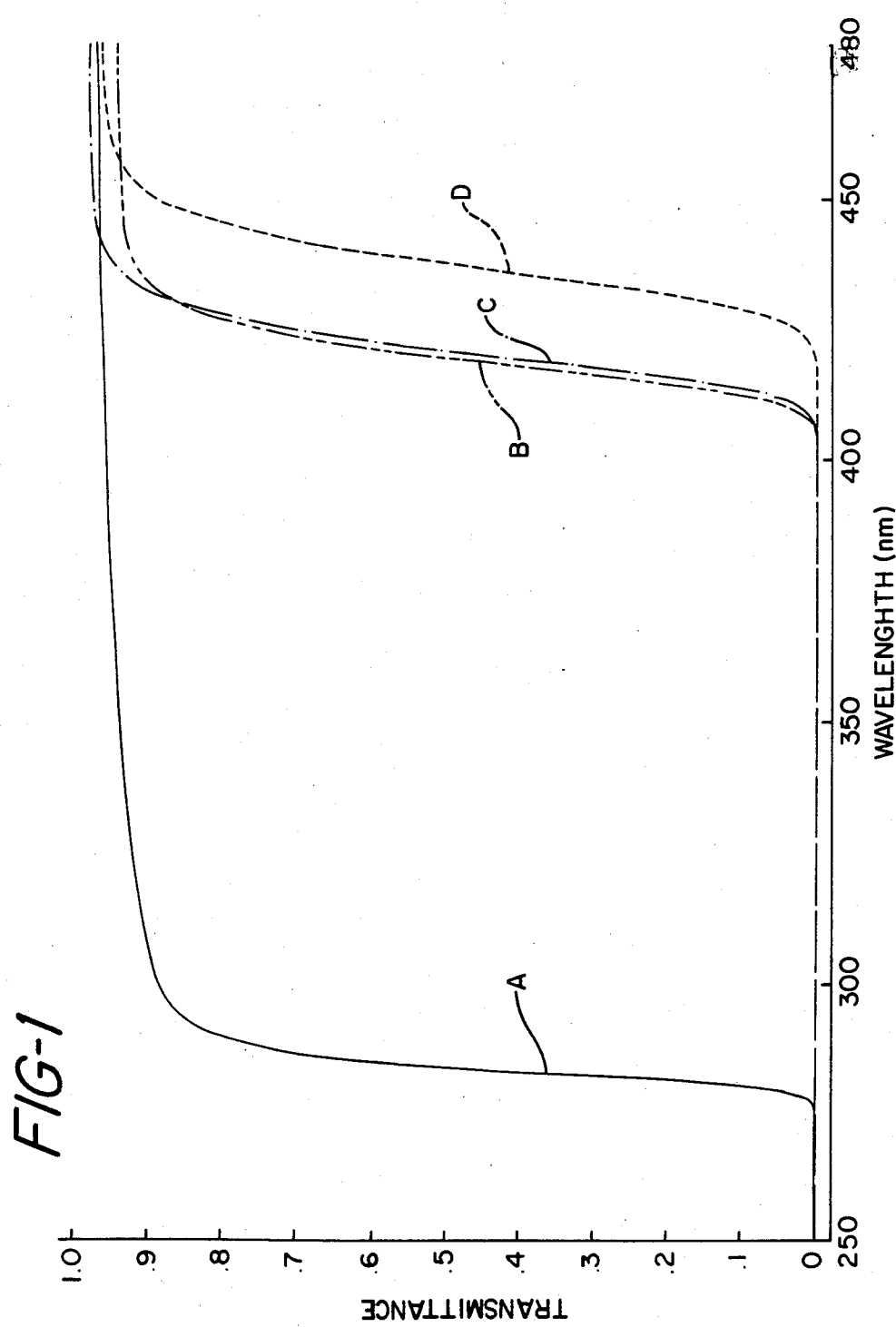
FIG. 1 is a plot of transmittance versus wavelength for certain silicone polymers of the invention compared with a conventional silicone polymer.

A glass beaker was charged with 9.12 g of Part A of a fast cure silicone RTV (McGhan Nusil Corporation, CF5-6810, addition reaction type) and 0.0365 g of monomer IV (Example 3). The contents were heated to 90° C. until the monomer melted, and were then mixed thoroughly with a glass rod. After cooling the mixture to ambient temperature (approximately 20° C.), 9.12 g of Part B of the silicone RTV was added and mixed thoroughly. (Standard mixing ratio is 1 part by weight of Part A to 1 part by weight of Part B.) The resulting mixture was deaerated under vacuum (approximately 600 Pa) and cured at 60° C. for 15 minutes in a mold into a 2 mm thick film using a Carver press at 1 MPa. The transmittance curve of the film (in water or saline) is shown in FIG. 1, as Curve C. Curve A is the transmittance curve of the pure cured silicone (CF5-6810) (in water or saline), i.e., containing none of the monomers of the invention. The film of this Example 10 was extracted with methylene chloride and the HPLC analysis of the extract did not show any detectable amount of monomer IV.

EXAMPLE 11

The procedures of Example 10 were followed using monomer X (Example 9) in place of monomer IV. The transmittance curve of the resulting (in water or saline) film is shown in FIG. 1 (Curve B). The HPLC analysis showed 0.032%, by weight, of monomer remaining in the cured film.

EXAMPLE 12

The procedures of Example 10 were followed using monomer XI (Example 4) in place of monomer IV. The transmittance curve of the resulting film (in water or saline) is shown in FIG. 1 (Curve D). The HPLC analysis showed no detectable amount of monomer XI in the film.

EXAMPLE 13

0.22 parts of monomer IV (Example 3) was dissolved in 100 parts of Part A of a (slow cure) silicone RTV (McGhan Nusil Corporation, MED-6810, addition reaction type) at 90°-100° C. After cooling the mixture to ambient temperature, 10 parts of Part B of the silicone RTV was added and mixed thoroughly. (The standard mixing ratio is 10 parts by weight of Part A to 1 part by weight of Part B.) The resulting mixture was degased for 75 minutes under vacuum (approximately 600 Pa) and cured at 140° C. for 15 minutes in a mold into 140 mm×140 mm×2 mm films using a Carver press at 1 MPa. The film showed transmittance of 0.9909 at 700 nm, 0.4536 at 420 nm and 0.0017 at 400 nm in 0.9% saline solution, tensile strength of 708±79 psi (4.88±0.54 MPa) and elongation at break of 151±11%.

EXAMPLE 14

The procedures of Example 13 were followed using 0.55 parts of monomer IV in place ov 0.22 parts of monomer IV. The resulting film showed transmittance of 0.9953 at 700 nm, 0.1160 at 420 nm and 0.0012 at 400 nm in 0.9% saline solution. The HPLC analysis showed no monomer IV remaining in the cured film.

EXAMPLE 15

A test tube was charged with 0.60 g of monomer IV (Example 3), 2.00 g of ethyl acrylate, 17.40 g of methyl methacrylate, 0.12 g of stearic acid, 0.025 g of lauroyl peroxide, and 111 microliters of 1-dodecanethiol. After all solid ingredients were dissolved, argon gas was bubbled into the mixture for about 20 seconds. The solution was the filtered through a polytetrafluorethylene (PTFE) membrane (pore size: 0.2 micrometers) and placed in a borosilicate glass tube under an argon straem. The tube was closed with a PTFE-coated cap and was placed in an air circulated oven (temperature program: 60° C., 16 hours; 60° C. heated up to 110° C., 2 hours; 110° C., 16 hours; 110° C. cooled to 20° C., 9 hours) to give a polymer (inherent viscosity: 0.37 dL/g at 0.5 g/dL in methylene chloride at 30° C.). The GC and HPLC analyses of the polymer showed residual monomers: 0.814% of ethyl acrylate; 0.840% of methyl methacrylate, and 2.07% of monomer IV. A 1 mm thick film of the polymer (prepared by hot-pressing at 200° C. and 2.9 MPa) showed transmittance of 0.9353 at 700 nm, 0.1506 at 430 nm, and 0.0008 at 400 nm in air.

What is claimed is:

1. A vinylsilylalkoxy arylbenzotriazole compound of the formula:

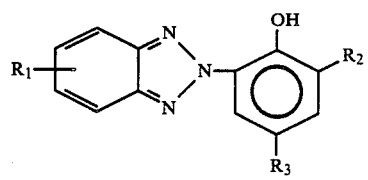

wherein $R_1$ and $R_3$ individually represent hydrogen, halo, alkoxy of up to 6 carbon atoms, or X, wherein $R_2$ represents hydrogen or alkyl of up to six carbon atoms, and wherein X represents a group of the formula:

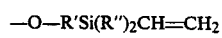

$$-O-R'Si(R'')_2CH=CH_2$$

wherein R' represents alkylene of from 1 to 10 carbon atoms, and wherein each R'' individually represents alkyl of up to 4 carbon atoms or aryl, provided that one, and only one, of $R_1$ or $R_3$ represents X.

2. The compound of claim 1 wherein said compound is 2-[3'-t-butyl-5'-(3''-dimethylvinylsilylpropoxy)-2'-hydroxyphenyl]-5-methoxybenzotriazole.

3. The compound of claim 1 wherein siad compound is 2-[3'-t-butyl-5'-(3''-dimethylvinylsilylpropoxy)-2'-hydroxyphenyl]-5-chlorobenzotriazole.

4. The compound of claim 1 wherein said compound is 2-(3'-t-butyl-2'-hydroxy-5'-methoxyphenyl)-5-(3''-dimethylvinylsilylpropoxy)benzotriazole.

5. An optically clear siloxane polymer having ultraviolet light absorbing properties, said polymer having covalently bonded therein the compound of claim 1.

6. An optically clear siloxane polymer having ultraviolet light absorbing properties, said polymer having covalently bonded therein the compound of claim 2.

7. An optically clear siloxane polymer having ultraviolet light absorbing properties, said polymer having covalently bonded therein the compound of claim 3.

8. An optically clear siloxane polymer having ultraviolet light absorbing properties, said polymer having covalently bonded therein the compound of claim 4.

9. The optically clear polymer of claim 5 in the form of an intraocular lens.

10. The optically clear polymer of claim 6 in the form of an intraocular lens.

11. The optically clear polymer of claim 7 in the form of an intraocular lens.

12. The optically clear polymer of claim 8 in the form of an intraocular lens.

* * * * *